US008238518B2

(12) United States Patent  
Poludniowski et al.

(10) Patent No.: US 8,238,518 B2  
(45) Date of Patent: Aug. 7, 2012

(54) RADIOTHERAPY SYSTEM

(75) Inventors: Gavin George Poludniowski, Surrey (GB); Michael David Ross Thomas, Surrey (GB)

(73) Assignee: The Institute of Cancer Research, London (GB)

( * ) Notice: Subject to any disclaimer, the term of this patent is extended or adjusted under 35 U.S.C. 154(b) by 0 days.

(21) Appl. No.: 12/821,672

(22) Filed: Jun. 23, 2010

(65) Prior Publication Data

US 2011/0317895 A1    Dec. 29, 2011

(51) Int. Cl.  
*A61N 5/10* (2006.01)  
*A61B 6/00* (2006.01)

(52) U.S. Cl. .................. 378/65; 378/4; 378/64

(58) Field of Classification Search .......... 378/4, 64, 378/65, 147–153  
See application file for complete search history.

(56) References Cited

U.S. PATENT DOCUMENTS

| | | | | |
|---|---|---|---|---|
| 4,550,371 | A * | 10/1985 | Glover et al. | 378/4 |
| 5,053,958 | A * | 10/1991 | Tam | 378/4 |
| 5,818,902 | A | 10/1998 | Yu | |
| 6,345,114 | B1 * | 2/2002 | Mackie et al. | 382/132 |
| 7,440,545 | B2 * | 10/2008 | Kidani et al. | 378/65 |
| 2003/0058994 | A1 * | 3/2003 | Sembritzki | 378/108 |
| 2003/0076927 | A1 * | 4/2003 | Nakashima et al. | 378/65 |
| 2003/0086526 | A1 * | 5/2003 | Clark et al. | 378/64 |
| 2003/0086530 | A1 * | 5/2003 | Otto | 378/65 |
| 2006/0039536 | A1 * | 2/2006 | Nishide et al. | 378/151 |
| 2006/0104407 | A1 * | 5/2006 | Zamyatin et al. | 378/4 |
| 2007/0297565 | A1 * | 12/2007 | Wofford et al. | 378/65 |
| 2009/0003512 | A1 * | 1/2009 | Pouliot et al. | 378/4 |
| 2010/0119032 | A1 | 5/2010 | Yan et al. | |
| 2011/0013742 | A1 * | 1/2011 | Zaiki et al. | 378/15 |

FOREIGN PATENT DOCUMENTS

WO    2006030181 A1    3/2006

OTHER PUBLICATIONS

Chen et al., Dose-guided radiation therapy with megavoltage cone-beam CT, The British Journal of Radiology, 79, 2006, pp. S87-S98.*  
Ansbacher et al., An evaluation of cine-mode 3D portal image dosimetry for Volumetric Modulation Arc Therapy, Journal of Physics: Conference Series, 250, 2010, pp. 1-4.*

(Continued)

*Primary Examiner* — Alexander H Taningco  
(74) *Attorney, Agent, or Firm* — Westman, Champlin & Kelly, P.A.; Z. Peter Sawicki (57) ABSTRACT

A radiotherapy system is disclosed, comprising a support for supporting a patient undergoing radiotherapy treatment, a gantry that is rotatable about an axis, a source of radiation mounted on the gantry and producing a beam of radiation directed towards a target region of the patient, a collimator coupled to said radiation source for collimating said radiation beam, the collimator comprising a plurality of beam-limiting elements, each movable to collectively define a shaped aperture through which the radiation beam passes, a portal imager mounted on the gantry opposite the radiation source for detecting the radiation after it has passed through the patient and generating corresponding images, and associated circuitry for controlling at least the gantry, the source, the collimator, and the portal imager, collating detected data comprising a plurality of images acquired from the imager including images at a plurality of angles of rotation of said gantry and images at a plurality of collimator shapes, and generating a three-dimensional image of the target region based thereon.

2 Claims, 3 Drawing Sheets

OTHER PUBLICATIONS

Anastasio, M.A., et al., "A preliminary investigation of local tomography for megavoltage CT imaging", Medical Physics, 2003, vol. 30, No. 11, pp. 2969-2980.

Bedford, J., "Treatment planning for volumetric modulated arc therapy", Medical Physics, 2009, vol. 36, No. 11, pp. 5128-5138.

Bedford, J.L., et al., "Treatment of lung cancer using volumetric modulated arc therapy and image guidance: a case study", 2008, Acta Oncol., vol. 47, No. 7, pp. 1438-1443.

Bortfeld, T., et al., "Single-arc IMRT?", Physics in Medicine and Biology, 2009, vol. 54, pp. N9-N20.

Burman, C., et al "TH-D-210A-02: Portal Imaging for Volumetric Modulated Arc Therapy", Medical Physics, 2009, Vol. No. 6, p. 2818.

Faridani, A., et al., "Introduction to Local Tomography", Radon Transforms and Tomography (Contemporary Mathematics, vol. 278, American Mathematical Society), ed, E.T. Quinto et al (Providence, Rhode Island) pp. 29-47, 2000.

Faridani, A., et al., "Local Tomography II", SIAM J. Appl. Math.. 1997, vol. 57, No. 4, pp. 1095-1127.

Faridani, A., et al., "Local Tomography", SIAM J. Appl. Math., 1992, vol. 52, No. 2, pp. 459-484.

Feldkamp, L.A., et al., "Practical cone-beam algorithm", J. Opt. Soc. Am. A/vol. 1, No. 6, pp. 612-619, 1984.

Iori, M., et al., "Dosimetric verification of IMAT delivery with a conventional EPID system and a commercial portal dose image prediction tool", Medical Physics, 2010, vol. 37, No. 1, pp. 377-390.

Kak, A. C., et al., Chapter 3: "Algorithms for reconstruction with nondiffracting sources", Principles of Computerized Tomographic Imaging (SIAM), 2001, (Philadelphia, USA), pp. 49-112.

Lewis, D.G., et al., "A megavoltage CT scanner for radiotherapy verification", Phys. Med. Biol., 1992, vol. 37, No. 10, pp. 1985-1999.

Liu, W., et al., "TH-C-303A-03: Real-Time Motion Detection of Prostate Target During Volumetric Arc Therapy Using Onboard Imaging Devices", Medical Physics, 2009, vol. 36, No. 6, p. 2800.

Mans, A., et al., "3D Dosimetric verification of volumetric-modulated arc therapy by portal dosimetry", Radiotherapy Oncology, 2010, vol. 94, pp. 181-187.

Mosleh-Shirazi, M.A., et al., "A cone-beam megavoltage CT scanner for treatment verification in conformal radiotherapy", Radiotherapy Oncology, 1998, vol. 48, No. 3, pp. 319-328.

Nakagawa, K., et al., "First clinical cone-beam CT imaging during volumetric modulated arc therapy" Radiotherapy and Oncology, 2009, vol. 90, pp. 422-423.

Ohnesorge, B., et al., "Efficient correction for CT image artifacts caused by objects extending outside the scan field of view", Medical Physics, 2000, vol. 27, No. 1, pp. 39-46.

Otto, K., "Volumetric Modulated Arc Therapy: IMRT in a single gantry arc", Medical Physics, 2008, vol. 35, No. 1, pp. 310-317.

Palma, D., et al., "Volumetric modulated arc therapy for delivery of prostate radiotherapy: comparison with intensity-modulated radiotherapy and three-dimensional conformal radiotherapy", Int. J. of radiation oncology, biology, physics, 2008, vol. 72, No. 4, pp. 996-1001.

Pouliot, J., "Megavoltage imaging, megavoltage cone beam CT and dose-guided radiation therapy", Front Radiat. Ther. Oncol., 2007, vol. 40, pp. 132-142.

Press, W. H., et al. Chapter B10: "Minimization or Maximization of Functions", Numerical recipes in Fortran 90 2nd Edition (Cambridge University Press) (New York, USA) pp. 1201-1204. 2002.

Ramachandran, G.N., et al., "Three dimensional reconstruction from radiographs and electron micrographs: applications of convolutions instead of Fourier transforms", Proc. Natl. Acad. Sci. USA, 1971, vol. 68, No. 9, pp. 2236-2240.

Ruchala, K.J, et al., "Megavoltage CT imaging as a by-product of multileaf collimator leakage", Phys. Med. Biol., 2000, vol. 45, pp. N61-N70.

Verbakel, W. F., et al., "Rapid delivery of stereotactic radiotherapy for peripheral lung tumors using volumetric intensity-modulated arcs", Radiotherapy and Oncology, 2009, vol. 93, pp. 122-124.

Webb, S., "Does the option to rotate the Elekta Beam Modulator MLC during VMAT IMRT delivery confer advantage?—a study of 'parked gaps'", Physics in Medicine Biology, 2010, vol. 55, No. 11, pp. N303-N319.

Webb, S. et al., "Some considerations concerning volume-modulated arc therapy: a stepping stone towards a general theory", Physic in Medicine Biology, 2009, vol. 54, No. 14, pp. 4345-4360.

Yi, B., et al., MO-FF-A1-01: "Fluoroscopic Verification of Intensity-Modulated Rotational Arc Therapy Delivery", Medical Physics, 2009, vol. 36, No. 6, p. 2708.

Yu, C.X., "Intensity-modulated arc therapy with dynamic multileaf collimation: An alternative to tomotherapy", Phys. Med. Biol., 1995, vol. 40, pp. 1435-1449.

Zhou, J., et al., SU-FF-J-81: "A Feasibility Study for Real-Time Tomosynthesis-Guided Rapid Arc Therapy", Medical Physics, 2009, vol. 36, No. 6, p. 2494.

European Search Report for Application EP11004568.9, Search completed Oct. 20, 2011.

Ruchala et al, "Megavoltage CT image reconstruction during tomotherapy treatments", Physics in Medicine and Biology, vol. 25, No. 12, Dec. 1, 2000, pp. 3545-3562.

Ford E.C. et al., "Cone-bean CT with megavoltage beams and an amorphous silicon electronic portal imaging device: Potential for verification of radiotherapy of lung cancer", Medical Physics, AIP, Melville, NY, vol. 29, No. 12, Dec. 1, 2000, pp. 2913-2924.

Hooper H.R. et al., "Technical note: Sinogram merging to compensate for truncation of projection data in tomotherapy imaging", Medical Physics, AIP, Melville, NY, vol. 29, No. 11, Nov. 1, 2002, pp. 2548-2551.

* cited by examiner

Fig. 3b

RADIOTHERAPY SYSTEM

FIELD OF THE INVENTION

The present invention relates to radiotherapy, and particularly relates to methods and apparatus for reconstructing three-dimensional images from portal images acquired during radiotherapy treatment.

BACKGROUND ART

It is known that exposure of human or animal tissue to ionising radiation will damage the cells thus exposed. This finds application in the treatment of pathological cells, for example. In order to treat tumours deep within the body of the patient, the radiation must however penetrate the healthy tissue in order to irradiate and destroy the pathological cells. In conventional radiation therapy, large volumes of healthy tissue can thus be exposed to harmful doses of radiation, potentially resulting in unacceptable side-effects. It is therefore desirable to design a device for treating a patient with ionising radiation and treatment protocols so as to expose the pathological tissue to a dose of radiation which will result in the death of those cells, whilst keeping the exposure of healthy tissue to a minimum.

Several methods have previously been employed to achieve the desired pathological cell-destroying exposure whilst keeping the exposure of healthy cells to a minimum. Many methods work by directing radiation at a tumour from a number of directions, either simultaneously from multiple sources or multiple exposures over time from a single movable source. The dose deposited from each direction is therefore less than would be required to destroy the tumour, but where the radiation beams from the multiple directions converge, the total dose of radiation is sufficient to be therapeutic. By providing radiation from multiple directions, the damage caused to surrounding healthy cells can be reduced.

Intensity modulated arc therapy (IMAT) is one method of achieving this, and is described in U.S. Pat. No. 5,818,902. In this process, the radiation source is rotated around the patient, and the radiation beam collimated to take a desired shape depending on the angle of rotation of the source, usually with a multi-leaf collimator (MLC). The potential advantages of a particular form of IMAT, volumetric modulated arc therapy (VMAT), have recently given rise to a number of commercial implementations and research studies. In these systems, the dose rate, rotation speed and MLC leaf positions may all vary during delivery. In general, plans comparable in quality and accuracy to static-gantry intensity-modulated radiotherapy (IMRT) can be obtained, normally with reduced delivery times.

To make sure the radiation beams are correctly directed, the treatment can be guided by imaging of the target region, before or even during the treatment. For example, kilovoltage computational tomography (CT) can be used during treatment by providing a separate source of imaging radiation mounted on the rotatable gantry, placed at an angle relative to the main radiation head. A detector is positioned diametrically opposite the source of imaging radiation, and collects imaging data for a plurality of rotational angles of the gantry. This data can then be reconstructed to form three-dimensional images using known CT techniques. See PCT application WO 2006/030181 for an example of this method. Kilovoltage radiation is preferred for imaging due to the high contrast between different structures in the patient.

An alternative method of imaging is to use the megavoltage radiation and an electronic imaging device. In this scheme, a radiation detector is placed on the rotatable gantry diametrically opposite the main treatment head, and is designed to detect the megavoltage radiation after it has passed through (and been attenuated by) the patient. The images generated are therefore individual transmission images, from the beam's eye view (BEV). Megavoltage imaging can be used to verify the position of the MLC leaves in relation to the target within the patient. The aperture thus created by the MLC leaves is known as a portal and hence this form of imaging is often called 'Portal imaging' and the detector an 'electronic portal imaging device' or EPID. However, the high energy associated with therapeutic radiation is not ideal for imaging purposes as the attenuation coefficients of the various tissue types within a patient are similar at this energy level, leading to poor image contrast. In addition, this method is inherently two-dimensional because in conventional radiotherapy the megavoltage beams are directed at the patient from typically two to nine angles, which may be insufficient to provide three-dimensional imaging.

It has been shown that CT reconstruction from megavoltage images (i.e. MVCT) is possible (see Pouliot J "Megavoltage imaging, megavoltage cone beam CT and dose-guided radiation therapy" 2007 *Frontiers of Radiation Therapy and Oncology* vol. 40, pp 132-42). However, for such reconstructions, the megavoltage images need to be obtained before or after the delivery of a treatment beam, using beams which generally encompass the anatomy that is desired to be imaged and are therefore not part of the radiation treatment. As this method does not make use of portal images acquired during treatment (i.e. those acquired with the varying MLC aperture of therapy) it is associated with an increase in undesired radiation dose to the patient.

A paper by Ruchala et al ("Megavoltage CT imaging as a by-product of multileaf collimator leakage", 2000 *Physics in Medicine and Biology*, vol. 45, pp N61-70) discloses a method of reconstructing three-dimensional CT images in tomotherapy. This process utilizes the leakage radiation through the closed leaves of a binary multi-leaf collimator (MLC), along with slight inefficiencies in treatment delivery, to generate MVCT images during treatment. However, the process is applicable only to tomotherapy, in which the leaves of the MLC are either open or closed, i.e. binary. The portal images for CT reconstruction are acquired only when all leaves of the MLC are in their closed positions, i.e. the leakage radiation used to create the images also generally encompasses the entire anatomy that is desired to be imaged.

What is required is an apparatus and a method for providing images of a target region in a patient during radiotherapy. Conventional kilovoltage CT scanning requires significant additional equipment (e.g. an extra source of radiation and a detector), leading to increased complexity and cost. Two-dimensional portal imaging suffers from reduced contrast between different internal structures, and it is frequently necessary to supplement it by larger and/or orthogonal images taken prior to or after treatment. Megavoltage CT and these other two approaches therefore increase the undesired dose applied to the patient. These techniques also potentially increase the time required to treat the patient as they represent an additional task for the operator to perform.

SUMMARY OF THE INVENTION

The present invention provides a method and apparatus for generating three-dimensional CT images of a target region in a patient during a rotational arc radiotherapy treatment. A portal imager detects the attenuated therapeutic radiation beam, and this data can be used to reconstruct a three-dimensional CT image. This technique avoids any additional radiation dose applied to the patient as the images are acquired simultaneously with the treatment delivery, thereby avoiding additional time for acquisition.

The application of a cone-beam formula to portal images acquired during a VMAT delivery does surprisingly lead to a readily recognizable CT volume. Further, local (lambda) tomography can be used to enhance the visual quality of the images. Such VMAT-CT reconstructions could be a useful tool for treatment position verification.

In one aspect of the present invention, there is provided a radiotherapy system, comprising a support for supporting a patient undergoing radiotherapy treatment, a gantry that is rotatable about an axis, a source of radiation mounted on the gantry and producing a beam of radiation directed towards a target region of the patient, a collimator coupled to said radiation source for collimating said radiation beam, the collimator comprising a plurality of beam-limiting elements, each movable to collectively define a shaped aperture through which the radiation beam passes, a portal imager mounted on the gantry opposite the radiation source for detecting the radiation after it has passed through the patient and generating corresponding images, and associated circuitry for controlling at least the gantry, the source, the collimator, and the portal imager, collating detected data comprising a plurality of images acquired from the imager including images at a plurality of angles of rotation of said gantry and images at a plurality of collimator shapes, and generating a three-dimensional image of the target region based thereon.

In an embodiment, the associated circuitry is configured to apply an algorithm to the detection data, reconstructing values of an attenuation coefficient for a plurality of locations in the target region.

The algorithm may set the attenuation coefficient to a null value for locations lying outside the radiation beam for more than a threshold range of angles of rotation of the gantry. In this way, the image is not degraded by attempting to reconstruct values for the attenuation coefficient for which there is insufficient data.

The algorithm may normalize the attenuation coefficient for each location according to the range of angular rotation of the gantry in which that location was in the radiation beam, thus taking into account the fact that locations may not fall within the beam's eye view for the complete $2\pi$ arc of the radiation source. In order to achieve this, the algorithm may comprise a masking function defining the positions of the MLC leaves.

The algorithm may extrapolate the detection data for locations falling outside of the radiation beam. One possible extrapolation scheme is to set a value for the detection data for locations extending beyond the edge of the radiation beam equal to the value for the detection data for the location at the edge of the radiation beam.

In certain embodiments, the algorithm may comprise a smoothing and deblurring function, which depends on detection data only for locations falling within a range of said location. Alternatively, the smoothing and deblurring function may be global, depending on all detection data for a particular dimension.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
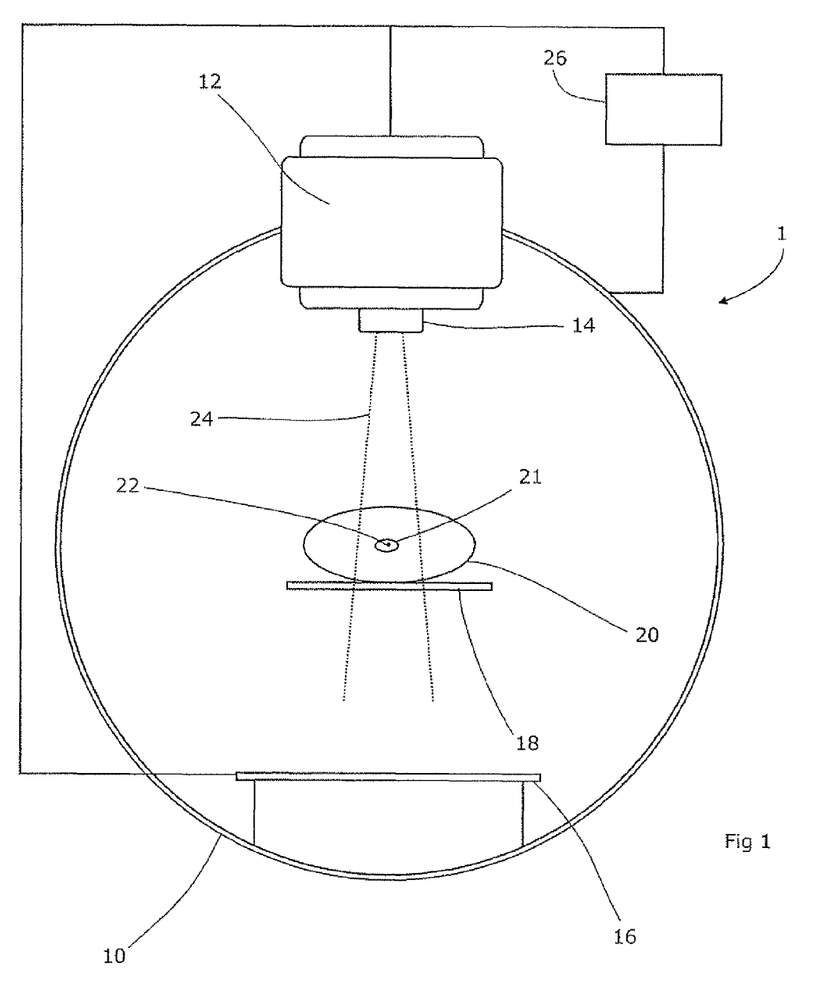
FIG. 1 is a schematic drawing of a radiotherapy system according to embodiments of the present invention.

FIG. 1 shows a radiotherapy system 1 according to embodiments of the present invention.

Structurally, the system is similar to a conventional radiotherapy apparatus. The system comprises a gantry 10 on which is mounted a source of radiation 12 and, diametrically opposite the source 12, a radiation detector 16. Such detectors are commonly referred to as portal imagers. The radiation source 12 is typically a linear accelerator producing x-rays or other penetrating radiation.

The gantry is rotatable about an axis 22. In the Figures, the gantry 10 is depicted as a ring-shaped support. Alternatively, however, the gantry may comprise a C-arm, with the source 12 and imager 16 on opposite arms. The isocentre of the system is defined as a plane running through the rotation axis 22 of the gantry 10 perpendicular to the instantaneous axis of the radiation beam.

A collimator 14 is coupled to the radiation source 12 in order to collimate and shape the radiation beam. That is, a first collimation of the radiation (not illustrated) takes place close to the source 12. This collimates the radiation produced by the source into a beam, e.g. a cone- or fan-shaped beam diverging away from the source. A further collimator 14 then acts on this collimated beam in order to shape the radiation as required for therapy. An example of a suitable collimator for this aspect is a multi-leaf collimator (MLC). Such devices comprise one or more banks of parallel leaves, each of which can be moved in a direction transverse to the radiation beam axis. The leaves are moveable into and out of the path of the radiation beam to a greater or lesser extent, and thus the combination of leaf positions collectively defines a shaped aperture through which radiation passes. In one embodiment, the MLC comprises two banks of leaves positioned on opposite sides of the radiation beam, with each leaf able to take any position with a range from outside the radiation beam to crossing the radiation beam. In order to sufficiently attenuate (i.e. block) the high-energy radiation, the leaves have a significant depth in a direction parallel to the radiation beam axis, and are manufactured from high atomic number materials such as tungsten. Thus, the output of the radiation source 12 and the collimator 14 is a shaped radiation beam 24 directed generally inwards towards the axis of rotation of the gantry.

Control and processing circuitry 26 is in communication with the gantry 10, the source 12 and the collimator 14 and controls their operation.

A patient 20 is positioned on a support 18 for treatment such that a treatment target 21 (e.g. a tumour) is placed at the isocentre of the system. The longitudinal axis of the support and, thus, the patient 20 usually but not necessarily lie substantially parallel to the rotation axis 22 of the gantry. Various processes and apparatus for positioning and locating the patient will be familiar to those skilled in the art. In one embodiment, the support allows linear translation of the patient in three dimensions. The support 18 may also allow for tilting and rotation of the patient 20, thus providing movement in up to six degrees of freedom (i.e. x, y, z, pitch, yaw and roll).

Figure 2:
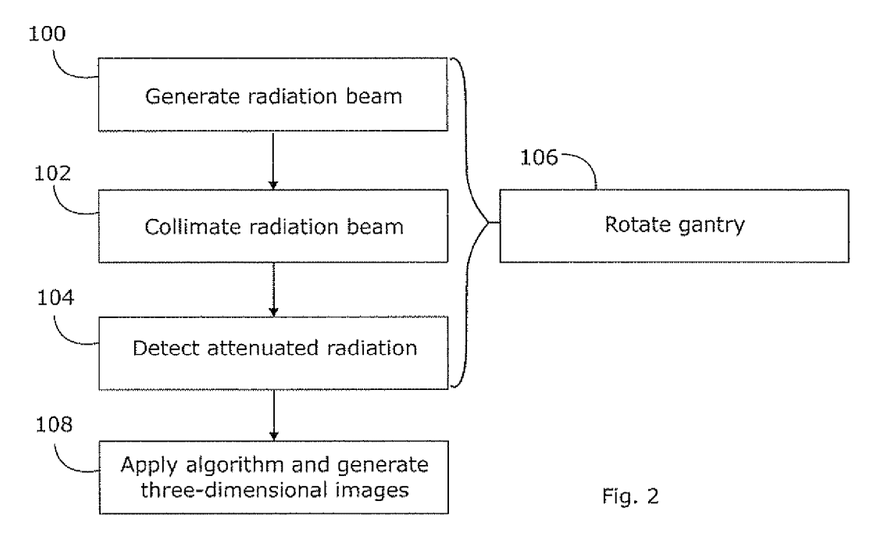
FIG. 2 is a flowchart of a method according to embodiments of the present invention.

In operation, the system 1 performs the method as set out in FIG. 2. The method begins once the patient has been positioned correctly, i.e. with the target at the isocentre.

Embodiments of the invention may also provide for motion of the patient during treatment. For example, the support 18 may compensate for movement of the patient due to the respiratory or cardiac cycles (i.e. minimizing the motion of the target 21 relative to the system 1). Similarly, the movement and positioning of the collimator leaves may compensate for such cyclical movement of the target 21. In the illustrated method, however, such processes are not considered for simplicity.

In step 100, the method begins with the radiation source 12 generating a radiation beam. The radiation itself may be x-rays or other penetrating radiation as required.

In step 102, the radiation beam is collimated by action of the collimator 14 to generate a shaped, collimated beam 24 for the purposes of therapy. For example, the beam may be shaped to conform to the shape of the target, or a part of the target, or any other shape to achieve a desired dose distribution in and around the target. This beam is incident on the patient 20 and, inevitably, some of the radiation is absorbed. The amount of absorption depends on the particular structures within the patient. In step 104, the attenuated radiation beam is detected by the portal imager 16. The detection signals are converted to data and provided to the control circuitry 26. These data sets largely comprise pixel data and can therefore (usually) be assembled into viewable images. They will therefore be referred to as "images" in this application, but this should not be interpreted to mean that the data sets must be stored in an image format, or that they must be viewed in an image form at any point. Often, the data sets will be transferred to the processor for conversion into CT datasets without ever being viewed in an image form.

Steps 100, 102 and 104 generally all take place while the gantry 10 rotates around the patient (step 106). Thus steps 100, 102, 104 and 106 may all take place substantially simultaneously. That is, the gantry 10 rotates around the patient, while the source 12 continuously generates a radiation beam and the collimator leaves move to new positions. The control circuitry 26 controls this operation, and may vary the radiation energy, the dose rate, the collimator positions and the speed of rotation of the gantry throughout the process.

The method then proceeds to step 108 in which the circuitry 26 applies an algorithm to the portal image data and reconstructs a three-dimensional CT image of the target region. There is no fixed time at which the algorithm is applied. The algorithm acts on the data that has been acquired up until the point the algorithm is invoked. If a three-dimensional CT image is required during treatment, the algorithm may be invoked during treatment. The CT image can then be used to guide the therapy for the remainder of the treatment. Alternatively, the CT image may be generated after treatment to assist the determination of the dosage distribution delivered to the patient, or to record the internal motion of the patient's tissues. Generally, however, the more data that is acquired, the better the quality of the CT image that is obtained.

The CT image so generated is a measure of the attenuation at any one point in three-dimensions within the target region. Thus, in one embodiment, the attenuation coefficient itself $f(r,\phi,z)$ is found (where $(r,\phi,z)$ are cylindrical polar coordinates). In alternative embodiments, the variable that is reconstructed may be an alternative quantity that is nonetheless related to the attenuation coefficient and provides useful imaging information. Hereinafter, the term "attenuation coefficient" is taken to mean the attenuation coefficient $f(r,\phi,z)$ as well as these related quantities.

The algorithm that is applied in step 108 allows the generation of a three-dimensional image from portal images despite many challenges. The portal images have a very narrow field of view of the target, as the collimator leaves act to block any radiation that is not directed towards the target in order to minimize the damage to surrounding healthy tissue. Moreover, the positions of the collimator leaves may change as the gantry rotates around the patient. Thus, the field of view at one angle of rotation will not in general be the same as the field of view in another angle of rotation.

The algorithm has several mathematical components, each of which act—both alone and in combination—to overcome these difficulties.

A first part of the algorithm relates to an acknowledgement that it may not be possible to reconstruct the attenuation coefficient for all locations within the target region. First, it is impossible to image locations that fall outside the target region entirely—and hence the path of the radiation beam at all gantry rotation angles. There simply is no data to reconstruct values from. However, there may be other locations within the target region which only fall within the path of the radiation beam for a subset of the gantry rotation angles. For these locations, there may nonetheless be insufficient data to reconstruct an accurate value for the attenuation coefficient. Reconstructing values of the attenuation coefficient for these locations may reduce the overall quality of the image. Thus, for each location within the target region, the first part of the algorithm sets the attenuation coefficient to a null value if that location falls outside the radiation beam for more than a threshold angular extent. For example, that threshold may be set at 270°. In that case, if a location lies inside the radiation beam for only 75° of the 360° revolution of the gantry, the attenuation coefficient for that location is set to null. The null value may be zero or any other value which in practice is regarded by the system as null.

A second part of the algorithm normalizes the reconstructed value of the attenuation coefficient for a particular location according to the angular range that location was inside the radiation beam. Thus, if a particular location lies within the radiation beam for a fraction of a complete revolution, the reconstructed attenuation coefficient for that location is divided by that fraction. For example, if the location lies within the radiation beam for 180° (i.e. half of the possible gantry angles), the value of the attenuation coefficient may be multiplied by two to account for this.

Both of these parts of the algorithm may employ a masking function to define the position of the collimator leaves at any particular rotation angle. In a plane orthogonal to the radiation beam axis, the masking function is equal to zero for locations that are blocked by the collimator leaves and one for locations that are open for radiation to travel through. The two variables used to define the location in that plane may be parallel and orthogonal respectively to the direction of travel of the collimator leaves, or at any angle with respect to the leaves.

Part of the algorithm is a measure of the energy received at the portal imager 16. Previously we have described that it may not be possible to reconstruct values of the attenuation coefficient for locations that lie outside, or partially outside, the radiation beam during rotation of the gantry. However, in order to reconstruct values for locations that lie inside the radiation beam, it may nonetheless be necessary to estimate values for the energy that would have been received by the portal imager for those locations that lie outside the radiation beam. That is, "would have been received" had the collimator leaves, for example, not blocked the radiation. The received energy values can be extrapolated to estimate the energy received at these locations outside the beam. One example is to set the received energy outside the right edge of the radiation beam equal to the received energy at the right edge of the radiation beam; likewise, the received energy outside the left edge of the radiation beam can be set equal to the received energy at the left edge of the radiation beam. Other extrapolation schemes are possible, however.

Finally, the reconstructed attenuation coefficient may be subject to a smoothing and de-blurring operation. The smoothing and de-blurring operation can be global, taking account of detected radiation across the whole field of view, or local, taking account only of detected radiation within a range of the location being considered. In the latter case, the requirement to extrapolate the received energy is reduced and therefore the accuracy of the reconstructed attenuation coefficient may be greater.

All of these features are embodied in the equation (14) described below. However, embodiments of the present invention may implement only one or more of the algorithm features described above in order to reconstruct attenuation coefficients from the portal images.

The present invention thus provides a method and an apparatus for reconstructing three-dimensional CT images from portal images acquired during treatment. Such a possibility was previously thought impossible due to the narrow and ever-changing field of view, and the incomplete angular coverage of the reconstruction points by the rotating radiation source (i.e. because of insufficient data). However, embodiments of the present invention can be greatly simplified compared to the imaging techniques commonly employed conventional radiotherapy systems, which typically require a separate kilovoltage source of radiation and detector.

APPENDIX

There now follows a mathematical description of the algorithm employed in step 108. The 'global' algorithm is shown in equation (10); the general algorithm, including the global and 'local' algorithms, is shown in equation (14). A hybrid version, designed to incorporate the benefits of both global and local algorithms, is shown in equation (16).

Figure 3A:
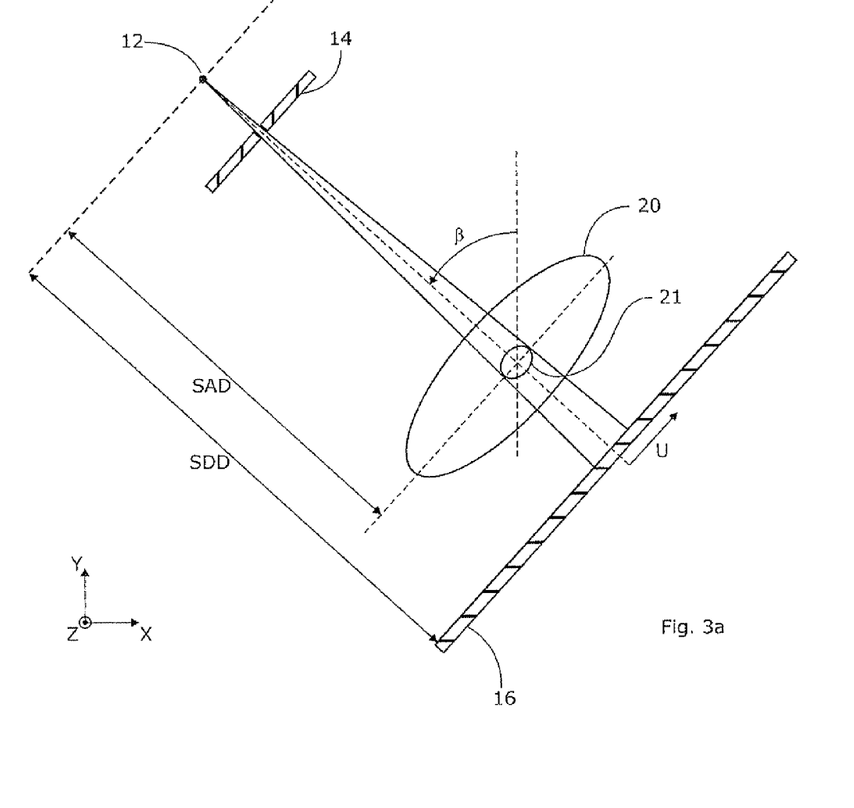
FIG. 3a shows the geometry of the radiotherapy system according to embodiments of the present invention.
Figure 3B:
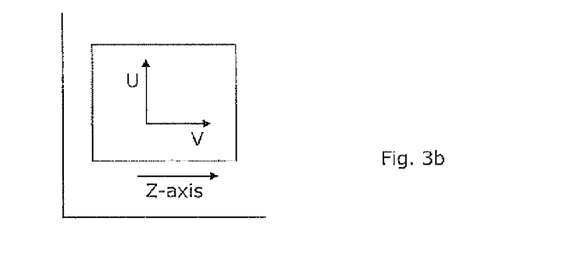
FIG. 3b shows the variables as seen from the beam's eye view.

There is denoted a 3D function describing the attenuation coefficient of a subject by the function, $f(r,\phi,z)$, where $(r,\phi,z)$ are cylindrical polar coordinates. In practice, either the Ram-Lak kernel (see Ramachandran G N and Lakshminarayanan A V 1971 "Three dimensional reconstruction from radiographs and electron micrographs: applications of convolutions instead of Fourier transforms" *Proceedings of the National Academy of Sciences US* vol 68, pp 2236-2240, the contents of which are incorporated herein by reference) or an apodizing kernel are applied in CT reconstruction. This results in the reconstruction not of $f(r,\phi,z)$ itself, but rather this function smoothed by a point-spread function (PSF). In the case of a Ram-Lak kernel this PSF arises only from the finite pixel-width. In the case of an apodizing kernel, additional smoothing may be included to reduce image noise. Consider such a reconstructed "image" in the $(r,\phi)$ plane. The smoothed 3D function, $f(r,\phi,z)$, can be expressed as, $$f_R(r,\phi,z) = E_R(r)^{**}f(r,\phi,z), \quad (1)$$

where $E_R(r)$ is a 2D PSF in the $(r,\phi)$ plane and  represents a 2D convolution operation. Now consider the cone-beam geometry illustrated in FIGS. 3***a* and 3*b*. The variables SAD and SDD are the source-to-axis distance and source-to-detector distance, respectively. The variable $\beta$ is the angle of the source with respect to the positive y-axis. The variables U and V denote the position of a point in the imaging plane. The Feldkamp cone-beam reconstruction algorithm (see Feldkamp L A, Davis L C and Kress J W 1984 "Practical cone-beam algorithm" *Journal of the Optical Society of America A* vol 1, pp 612-19, the contents of which are incorporated herein by reference) can then be written as, $$f_R(r,\phi,z) = \frac{1}{2}\int_0^{2\pi} d\beta \left(\frac{SAD}{SAD_{-s}}\right)^2 \quad (2)$$

$$\int_{-u_{max}}^{u_{max}} du D_\beta(u,v) e_R(u'-u)\left(\frac{SAD}{\sqrt{SAD^2+u^2+v^2}}\right),$$

where, $$u = U\left(\frac{SAD}{SDD}\right), \quad v = V\left(\frac{SAD}{SDD}\right), \quad (3)$$

$$u' = t\frac{SAD}{SAD-s} \quad (4)$$

$$t = r\cos(\phi-\beta), \quad s = r\sin(\phi-\beta) \quad (5)$$

and $D_\beta(u,v)$ is the cone-beam ray-projection at the point on the detector defined by $(u,v)$ for the source rotation, $\beta$. The function, $e_R(u)$, is related to the PSF and takes the form, $$e_R(u) \approx \frac{1}{2\pi}\Lambda\varepsilon_R(u) \quad (6)$$

where one possible form for $\varepsilon_R(u)$ is $$\varepsilon_R(u) = \frac{1}{R\sqrt{\pi}}\frac{\Gamma\left(\frac{5}{2}+\alpha\right)}{\Gamma(2+\alpha)}\left(1-\left(\frac{u}{R}\right)^2\right)^{\alpha+1}, \text{ if } |u|\leq R \quad (7)$$

$$= 0, \text{ otherwise}$$

where R defines a range and $\Lambda$ is the Calderon operator. The Calderon operator is pseudo-differential operator that performs a de-blurring operation. Consider a Euclidean space $\Re^n$ in which a point is defined by the vector, $\underline{r}$. A function in this space, $\varepsilon(\underline{u})$, may have a Fourier transform, $E(\underline{\rho})$, and a Fourier transform pair, $$E(\underline{\rho}) = F\{\varepsilon(\underline{u})\} \quad (8)$$

$$= \int_{\Re^n} e^{+2\pi i\underline{u}\cdot\underline{\rho}}\varepsilon(\underline{u})$$

and $$\varepsilon(\underline{u}) = F^{-1}\{E(\underline{\rho})\}$$

$$= \int_{\Re^n} e^{+2\pi i\underline{u}\cdot\underline{\rho}}E(\underline{\rho}).$$

The Calderon operator, acting on a function $\varepsilon(\underline{u})$, is then defined as $$\Lambda\varepsilon(\underline{u}) = F^{-1}\{2\pi|\rho|F\{\varepsilon(\underline{u})\}\}, \quad (9)$$

where $\Lambda$ acts on the n-dimensional space. In expression (6) the Calderon operator acts on the scalar variable u only (i.e. n=1). Note that it would also be possible to define $\bar{e}_R(u)$ as a standard global CT convolution kernel, such as the Ram-Lak or Hamming kernel. This would, however, preclude the extension to local (lambda) reconstruction discussed subsequently.

Returning to equation (2), it is noted that the factors appearing in the round-brackets of this expression are geometric weighting factors. It is assumed for simplicity that SAD>>u,v and ignore such factors: this simplifies the resulting formulae. Equation (2), however, is inadequate, as it stands, in dealing with the data insufficiencies in the projection data. The following VMAT-CT formula is therefore proposed, $$f_R(r,\phi,z) \approx \frac{1}{2} \frac{\Theta\left(\int_0^{2\pi} M_\beta(u',v)d\beta - \beta'\right)}{\frac{1}{2\pi}\int_0^{2\pi} M_\beta(u',v)d\beta} \quad (10)$$

$$\int_0^{2\pi}\left[M_\beta(u',v)\int_{-u_{max}}^{u_{max}} duD_\beta^{extrap}(u,v)e_R(u'-u)\right]d\beta,$$

where the extra constituents are defined in detail below. The MLC aperture is described by the masking function, $M_\beta(u,v)$. If the aperture extent, at a particular v, and $\beta$ is defined by the interval, $u_1(v,\beta)<u<u_2(v,\beta)$, then a possible form for the masking function is $$M_\beta(u,v) = \begin{cases} 1, & \text{if } u_1(v,\beta) < u < u_2(v,\beta) \\ 0, & \text{otherwise.} \end{cases} \quad (11)$$

The acquired ray-projections should be extrapolated for the purposes of the convolution integral in (10). One possible extrapolation scheme is:

$$D_\beta^{extrap}(u,v) = \begin{cases} D_\beta(u,v), & \text{if } u_1(v,\beta) \leq u \leq u_2(v,\beta) \\ D_\beta(u_1,v), & \text{if } u < u_1(v,\beta) \\ D_\beta(u_2,v), & \text{if } u > u_2(v,\beta). \end{cases} \quad (12)$$

More sophisticated extrapolation schemes are, of course, possible. This makes no assumption about specific MLC orientation. However, with some collimator rotations (e.g. 90°) it would be possible for leaves to split the aperture into more than a single region in the u-direction. Such cases (not considered here) would require a slightly more complex masking function and extrapolation. The masking function is included inside the back-projection integral to prevent the back-projection of convolved ray-projections outside of the BEV. However, to obtain imaging data of the target region, it is not important if the data set is not strictly complete over an angular range. That said, where the data is woefully insufficient the image quality will suffer, and thus a cut-off radian coverage, $\beta'$, may be included. This parameter appears in the Heaviside step-function, $\Theta(\ldots)$, of equation (10). The Heaviside function forces the reconstructed value to zero at positions in the BEV for less than $\beta'$ radians. This allows the elimination of reconstruction points for which so little data are available that they are likely to be misleading. The denominator of the fraction in which the Heaviside function appears is present to normalise the contributions according to the angular extent of data available. Thus, for example, a voxel in the BEV for 75% of the $2\pi$ arc $$\left(\text{i.e. } \frac{1}{2\pi}\int_0^{2\pi} M_\beta(u',v)d\beta = 0.75\right),$$

will be divided by a factor 0.75 to approximately correct for the missing contributions.

Due to data-insufficiencies in the set of projections obtained in a VMAT treatment, exact and unique reconstruction of $f_R(r,\phi,z)$ may not be possible. The data-insufficiency in the VMAT-CT problem, in particular, the width truncation of projections by the MLC, suggests the possibility of using local tomography techniques (see Faridani A, Ritman E L and Smith K T 1992 "Local Tomography" SIAM *Journal of Applied Mathematics* vol 52, pp 459-484, the contents of which are incorporated herein by reference). The idea of local (lambda) CT is not to reconstruct $f_R(r,\phi,z)$ but rather a related object, $$\Lambda^m f_R(r,\phi,z) \quad (13)$$

where m is an integer denoting the number of repeat operations of the Calderon operator. It is noted that in (13), $\Lambda$ acts on the n=2 space of $(r,\phi)$ (but not over z). The new object (13) has many of the same properties as the original attenuation coefficient function. The generalised version of the VMAT-CT reconstruction formula is then, $$\Lambda^m f_R(r,\phi,z) \approx \frac{1}{2} \frac{\Theta\left(\int_0^{2\pi} M_\beta(u',v)d\beta - \beta'\right)}{\frac{1}{2\pi}\int_0^{2\pi} M_\beta(u',v)d\beta} \quad (14)$$

$$\int_0^{2\pi}\left[M_\beta(u',v)\int_{-u_{max}}^{u_{max}} duD_\beta^{extrap}(u,v)e_R^{(m)}(u'-u)\right]d\beta,$$

where the generalized function $e_R^{(m)}(u)$ is $$e_R^{(m)}(u) \approx \frac{1}{2\pi}\Lambda^{m+1}\varepsilon_R(u). \quad (15)$$

If m is even, such as the m=0 case, $e_R^{(m)}(u)$ has a non-compact support and is termed "global". The convolved ray-projection, to be back-projected, then depends on every unconvolved ray-projection along the u integration direction, for fixed values of v. Therefore, if the patient does not entirely fit within the field-of-view at any angle $\beta$, required data are absent. Despite this, in some cases, the ray-projections through the patient outside the acquired set can be extrapolated reliably enough to provide an acceptable reconstruction. It can be shown, however, that if $m \geq -1$ and odd then $e_R^{(m)}(u)$ can have a compact support and be described as "local". This means that a convolved ray-projection, to be back-projected, depends only on the unconvolved ray-projections in its local vicinity (within a distance R in fact). Thus the m=1 algorithm has less restrictive data requirements than the m=0 case. In some cases therefore we might expect local tomography (m=1) to provide more useful information than the global (m=0) algorithm.

To encapsulate the benefits of either approach (local or global tomography) a hybrid semi-local construction is proposed, $$\Sigma_\sigma f_R(r,\phi,z) = f_R(r,\phi,z) + \sigma R \Lambda f_R(r,\phi,z), \quad (16)$$

where σ is a dimensionless parameter and R is again the range parameter.

It will of course be understood that many variations may be made to the above-described embodiment without departing from the scope of the present invention.

Although the present invention has been described with reference to preferred embodiments, workers skilled in the art will recognize that changes may be made in form and detail without departing from the spirit and scope of the invention.

The invention claimed is:

1. A radiotherapy system, comprising:
 a support for supporting a patient undergoing radiotherapy treatment;
 a gantry, rotatable about an axis;
 a source of radiation, mounted on the gantry, producing a beam of radiation directed towards a target region of the patient;
 a collimator, coupled to said radiation source, for collimating said radiation beam, the collimator comprising a plurality of beam-limiting elements, moveable to collectively define a shaped aperture through which the radiation beam passes;
 a portal imager, mounted on the gantry opposite the radiation source, for detecting the radiation after it has passed through the patient and generating corresponding images; and associated circuitry, for
   i. controlling at least the gantry, the source, the collimator, and the portal imager,
   ii. collating detected data comprising a plurality of images acquired from the imager, the plurality including images at a plurality of angles of rotation of said gantry and images at a plurality of collimator shapes, and
   iii. generating a three-dimensional image of the target region based thereon,
 wherein an algorithm sets the attenuation coefficient to a null value for locations lying outside the radiation beam for more than a threshold range of angles of rotation of the gantry.

2. A method of generating three-dimensional images of a target region within a patient, in a system comprising a rotatable gantry, a source of radiation mounted on the gantry for producing a beam of radiation, a multi-leaf collimator for collimating the radiation beam, and a detector mounted on the gantry opposite the source, the method comprising the steps of:
 for a plurality of angles of rotation of the gantry, detecting an attenuated radiation beam after it has passed through the target region, the radiation beam being collimated into a first shape for a first angle of rotation, and a second, different shape for a second angle of rotation;
 collating detection data corresponding to the detected attenuated radiation beam for said plurality of angles of rotation of said gantry; and
 generating a three-dimensional image of the target region based on the collated detection data,
 wherein an algorithm sets the attenuation coefficient to a null value for locations lying outside the radiation beam for more than a threshold range of angles of rotation of the gantry.

* * * * *